United States Patent [19]

Wilson et al.

[11] 4,309,548

[45] Jan. 5, 1982

[54] CHLORINATION OF 2-CHLORO-5-TRICHLOROMETHYLPYRIDINE

[75] Inventors: Charles A. Wilson, Pittsburg; John A. Werner, Antioch, both of Calif.

[73] Assignee: The Dow Chemical Company, Midland, Mich.

[21] Appl. No.: 225,824

[22] Filed: Jan. 19, 1981

[51] Int. Cl.³ .......................................... C07D 213/26
[52] U.S. Cl. .................................................. 546/345
[58] Field of Search ................................ 546/345, 346

[56] References Cited

U.S. PATENT DOCUMENTS 3,186,994  6/1965  Johnston et al. .................... 546/345

Primary Examiner—Alan L. Rotman
Attorney, Agent, or Firm—S. Preston Jones; Ronald G. Brookens

[57] ABSTRACT 2,3-Dichloro-5-trichloromethylpyridine is produced by selective liquid phase chlorination of 2-chloro-5-trichloromethylpyridine.

4 Claims, No Drawings

CHLORINATION OF 2-CHLORO-5-TRICHLOROMETHYLPYRIDINE

BACKGROUND OF THE INVENTION

The compound 2,3-dichloro-5-trichloromethylpyridine is a useful intermediate in the preparation of various trichloromethyl pyridine ethers which have agricultural applications as parasiticides. See U.S. Pat. No. 3,244,722. Certain pyridinyloxyphenoxy alkanoic acids also display desirable herbicidal activity in the control of grassy weeds. One convenient method for preparing this group of compounds is by the fluorination of the trichloromethyl on 2,3-dichloro-5-trichloromethylpyridine followed by reaction with a hydroxy-substituted phenoxy alkanoic acid. Unfortunately, an easy method for preparing this intermediate in good yields has not been previously available. The present invention is directed to a liquid phase chlorination in which a chlorine substituent is selectively added to the 3- position of the compound 2-chloro-5-trichloromethylpyridine.

SUMMARY OF THE INVENTION

This invention relates to a process for preparing 2,3-dichloro-5-trichloromethylpyridine by liquid phase chlorination which comprises treating a mixture containing 2-chloro-5-trichloromethylpyridine and a solvent or solvent mixture principally composed of N-methylpyrollidone, N,N-dimethylformamide, or dimethylsulfoxide with an excess amount of chlorine at a temperature of from about 55° C. to about 120° C. for a time sufficient to chlorinate at least some of the 2-chloro-5-trichloromethylpyridine in the 3- position of the pyridine ring.

In carrying out the selective liquid phase chlorination that is the subject of this invention, excess chlorine is employed, i.e., an amount of chlorine in excess of the stoichiometric amount required to chlorinate the 3- position of the pyridine ring. Thus, since one-half mole of chlorine gas is required to chlorinate each mole of starting material, an excess amount is at least one-half mole. For practical consideration, an excess of at least about 30% chlorine is employed with amounts greater than about 10 times the stoichiometric requirements being entirely satisfactory.

DETAILED DESCRIPTION OF THE INVENTION

In preparing the reaction mixture, a solvent or solvent mixture principally composed of one or more of N-methylpyrollidone, N,N-dimethylformamide, or dimethylsulfoxide must be used. The selected solvent is preferably present in at least equimolar amounts to the 2-chloro-5-trichloromethylpyridine. Amounts of solvent less than this amount will result in incomplete chlorination of the starting material and low yields. While the exact mechanism by which the selective chlorination of the 3- position is not known, it is believed that the solvent acts as an intermediary in the reaction. However, it is not desired to limit the invention to any particular mechanism in the absence of knowledge of the precise nature of the reactions taking place.

In carrying out the process, the chlorination proceeds satisfactorily within a temperature range of from about 55° C. to about 120° C., with a range of from about 90° C. to about 120° C. being preferred. The chlorination will proceed most rapidly at the higher temperatures of the range, with the chlorination occuring only slowly at the lower end of range.

The process may be carried out over a broad range of pressures. Pressures in excess of atmospheric may increase the rate of reaction, but for convenience the process is usually carried out at atmospheric pressure. The reaction does result in an exotherm which, unless controlled, will raise the temperature above the desired range. It has been found desirable to add a small quantity of water to the reaction mixture to control the temperature rise. The addition of from about 5 mole percent to about 15 mole percent water has generally been found satisfactory for controlling the exotherm.

The following examples will serve to further illustrate the invention, but are not to be construed as a limitation thereon.

EXAMPLE 1

In a 100 ml reaction vessel fitted with a condenser a mixture was prepared by adding 17.8 grams of N,N-dimethylformamide (0.24 mole) to 23.1 grams of 2-chloro-5-trichloromethyl pyridine (0.10 mole). The reaction was stirred and chlorine gas introduced through a gas inlet tube. The temperature was maintained at about 115° C. for in excess of 60 hours. Analysis by glc (gas/liquid chromatography) indicated 91% of the pyridine starting material had been converted to 2,3-dichloro-5-trichloromethylpyridine.

EXAMPLE 2

A mixture was prepared containing 23.1 grams of 2-chloro-5-trichloromethylpyridine (0.1 mole), 18.3 grams of N,N-dimethylformamide (0.25 mole) and 0.2 grams of water (11 mmole). The temperature of the mixture was raised to 90°-95° C. and chlorine slowly added. The reaction was continued for about 90 hours. Analysis by glc indicated 75% of the pyridine starting material had been chlorinated to 2,3-dichloro-5-trichloromethylpyridine.

What is claimed is:

1. A process for preparing 2,3-dichloro-5-trichloromethylpyridine which comprises treating a reaction mixture containing 2-chloro-5-trichloromethylpyridine and a solvent or solvent mixture principally composed of N-methylpyrollidone, N,N-dimethylformamide, or dimethylsulfoxide with an excess amount of chlorine at a temperature of from about 55° C. to about 120° C. for a time sufficient to chlorinate at least some of the 2-chloro-5-trichloromethylpyridine to form 2,3-dichloro-5-trichloromethylpyridine.

2. The process of claim 1 wherein the solvent is principally N,N-dimethylformamide.

3. The process of claim 2 wherein the reaction mixture contains from about 5 mole percent to about 15 mole percent water.

4. The process of claim 2 wherein the temperature is from about 90° C. to about 120° C.

* * * * *